United States Patent [19]

Tavtigian et al.

[11] Patent Number: 5,789,206
[45] Date of Patent: Aug. 4, 1998

[54] METHOD FOR LIGATING ADAPTORS TO NUCLEIC ACIDS WHICH METHODS ARE USEFUL FOR OBTAINING THE ENDS OF GENES

[75] Inventors: Sean V. Tavtigian, Salt Lake City; Steven Stone, Midvale; Ping Jiang; Alexander Kamb, both of Salt Lake City, all of Utah

[73] Assignee: Myriad Genetics, Inc., Salt Lake City, Utah

[21] Appl. No.: 499,787

[22] Filed: Jul. 7, 1995

[51] Int. Cl.$^6$ ............................................. C12P 19/34
[52] U.S. Cl. ................ 435/91.2; 435/91.52; 935/77; 935/78
[58] Field of Search .............. 435/6, 91.2, 91.21, 435/24.32, 91.52

[56] References Cited

U.S. PATENT DOCUMENTS 4,935,357  6/1990  Szybalski ........................... 435/91.2

OTHER PUBLICATIONS

Fors et al. (1990) Nucl. Acid Res. 18(9) 2793–2799.
Sugimoto et al. (1991) Agric. Biol. Chem. 55 (11) 2687–2692.
Fromont Racine et al. Nucl Acid Res. (1993) 21(7):1683–1684.
Philippe et al. Biochem. Biophys. Res. Comm. (1992) 188(2):843–850.
1988–1989 New England Biolabs Catalog, p. 66., Beverly, MA.
Liu, X. and Gorovsky, M.A. (1993). "Mapping the 5' and 3' ends of *Tetrahymena thermophila* mRNAs using RNA ligase mediated amplification of cDNA ends (RLM–RACE)," *Nucl. Acids Res.* 21:4954–4960.
Frohman, M.A. et al. (1988). "Rapid production of full–length cDNAs from rare transcripts: Amplification using a single gene–specific oligonucleotide primer," *Proc. Natl. Acad. Sci. USA* 85:8998–9002.

Soh, J. and Pestka, S. (1992). "Hybrid Selection of mRNA with Biotinylated DNA," *Methods in Enzymology* 216:186–196.
Barlet, V. et al. (1994). "Quantitative detection of hepatitis B virus DNA in serum using chemiluminescence: comparison with radioactive solution hybridization assay," *J. Virol. Meth.* 49:141–152.
Jansen, R.W. et al. (1993). "High–Capacity In Vitro Assessment of Anti–Hepatitis B Virus Compound Selectivity by a Virion–Specific Polymerase Chain Reaction Assay," *Antimicrobial Agents and Chemotherapy* 37:441–447.

(List continued on next page.)

*Primary Examiner*—Lisa B. Arthur
*Attorney, Agent, or Firm*—Rothwell, Figg, Ernst & Kurz, P.C.

[57] ABSTRACT

The present invention is directed to cloning the ends of genes. Traditionally it has been very difficult to recover the 5' end of a gene. The present invention greatly eases this problem. The invention is a variation on RACE and uses a combination of techniques. Specific genes are purified by using three enrichment steps—1) a polymerase chain reaction, 2) a hybrid capture step, and 3) a second polymerase chain reaction. The inclusion of the hybrid capture step results in a greater enrichment than occurs with RACE. The ends of the gene are retained by use of a novel technique of attaching adaptors at the ends of the nucleic. The 5' end of the gene is conserved by preparing a first strand of cDNA and ligating to this an adaptor which is partially double stranded wherein the overhang or single stranded region of the adaptor is degenerate which allows for a fraction of the adaptor population to hybridize with the first strand of cDNA at the 3' end of the cDNA. This hybridization holds the adaptor in conjunction with the cDNA during the ligation step thereby resulting in a highly efficient ligation. The unique portion of the adaptor is used to design an oligomer to prime the second strand synthesis. None of the 5' sequence is lost in this method thereby allowing for a greater possibility of recovering the extreme 5' end of the gene.

2 Claims, 5 Drawing Sheets

OTHER PUBLICATIONS

Saiki, R.K. et al. (1985). "Enzymatic Amplification of β–Globin Genomic Sequences and Restriction Site Analysis for Diagnosis of Sickle Cell Anemia," *Science* 230:1350–1354.

Mullis, K.B. and Faloona, F.A. (1987). "Specific Synthesis of DNA in Vitro via a Polymerase–Catalyzed Chain Reaction," *Methods in Enzymology* 155:335–350.

Saiki, R.K. et al. (1988). "Primer–Directed Enzymatic Amplification of DNA with a Thermostable DNA Polymerase," *Science* 239: 487–491.

Ruberti, F. et al. (1994). "The use of the RACE method to clone hybridoma cDNA when V region primers fail," *J. Immunol. Meth.* 173:33–39.

Skinner, T.L. et al. (1994). "Three different calmodulin–encoding cDNAs isolated by a modified 5'–RACE using degenerate oligodeoxyribonucleotide," *Gene* 151:247–251.

Chen, F. and Suttle, C.A. (1995). "Nested PCR with Three Highly Degenerate Primers for Amplification and Identification of DNA from Related Organisms," *BioTechniques* 18:609–611.

AMPLIFY WITH ANCHOR 2A AND GENE-SPECIFIC OLIGO #R1
GEL PURIFY SIZE FRACTION OR COLUMN FRACTIONATE

CAPTURE WITH NESTED, BIOTINYLATED GENE-SPECIFIC OLIGOMER

REAMPLIFY WITH ANCHOR 2B AND GENE-SPECIFIC OLIGOMER #2

METHOD FOR LIGATING ADAPTORS TO NUCLEIC ACIDS WHICH METHODS ARE USEFUL FOR OBTAINING THE ENDS OF GENES

BACKGROUND OF THE INVENTION

There is a tremendous interest in finding specific genes from organisms. This is especially true for genes implicated in diseases, although there is also much interest in other genes in general. Many techniques have been developed to identify and purify genes and then to analyze them. These include the whole range of techniques used in molecular biology such as DNA sequencing, protein sequencing, screening of genomic and cDNA libraries, chromosome mapping, amplification techniques as the polymerase chain reaction, etc., which are all well-known and widely used. Reasons for locating specific genes are numerous. One may simply want to clone the gene into a bacterial or yeast vector and use the bacterium or yeast as a factory to synthesize the gene product in large quantities. This allows for production of large quantities of the gene product which can then readily be purified. The classic examples are insulin and growth hormone. Another reason for desiring to locate a gene is to determine which gene is responsible for causing a specific disease. If this can be accomplished it may be possible to screen persons for a predisposition to the disease if it is found that the person contains a mutation in the gene. Another goal will be to perform gene therapy on persons found to have a genetic predisposition to the disease, although presently gene therapy is only in the very early stages of development. For either of these purposes, i.e., to clone genes for protein production or to identify genes associated with a disease, it is most desirable to determine the complete gene sequence. If one is missing a portion of the gene the goal may not be attained. If one does not have the 5' or 3' end of a gene which was cloned to produce the gene product then of course the complete protein product will not be produced and may be inactive. Similarly, if one is missing a portion of the gene associated with a disease one will not be able to analyze the missing portion of the gene for mutations. The ends of genes are also often involved in proper gene regulation and it is therefore important to have found these regions so that they can be analyzed.

Today it is recognized that most genes, at least in eukaryotic organisms and certainly in the "higher" eukaryotes such as mammals, have a complex structure in which the genes are divided into exons and introns. The exons are the regions which actually encode the final expressed gene product and also include some 5' and 3' DNA which does not actually encode a protein. The introns are regions of nucleic acid which are found intervening between the exons. The introns are transcribed into the initial RNA transcript known as heterogeneous RNA (HRNA) but these intronic regions of HRNA are cut out in a process called splicing to produce a messenger RNA (mRNA). The mRNA contains all of the coding sequences for the gene. This complex structure of introns and exons may result in a single gene being stretched out so that it covers several hundred thousand base pairs along the chromosome even though the coding region may be only a few thousand bases in length. An example of this is a gene responsible for some cases of breast cancer. This gene, named BRCA1, is split into 24 separate exons (Miki et al., *Science* 266:66–71 (1994)). The mRNA is approximately 7.8 kb and the coding region is 5589 nucleotides. This complexity of gene structure and the very large amount of DNA over which the gene may be stretched often makes it difficult to find the complete gene. In practice it has been especially difficult to locate the 5' ends of genes.

The present invention is directed at a method which makes it much simpler to locate the ends of any gene of interest for which at least a small amount of sequence data is already known. The invention combines a variety of known techniques in a novel manner and also adds a few new variations on these old techniques to accomplish this task by using each step to enrich further for the gene of interest. The method is a variation on a technique known as RACE (Rapid Amplification of cDNA Ends). One method used as part of the invention is the polymerase chain reaction which is used at two separate steps for amplification and enrichment purposes. A hybrid capture step is also included to enrich further for the gene of interest. Modifications have been included which increase the chances of having the 5' or 3' end of the gene included as part of the final amplified DNA product.

SUMMARY OF THE INVENTION

The invention is designed to synthesize cDNA in such a manner that the 5' or the 3' end of the cDNA is not lost. It has often been difficult to locate the 5' ends of genes and the present invention is one method which can solve this problem. Briefly stated, the invention is as follows: mRNA is purified and reverse transcribed using a tailed oligo dT primer plus an anchor or a tailed random dodecanucleotide as primer, the resulting heteroduplex is treated to remove the RNA strand. If one is interested in finding the 5' end of a gene, a novel technique is used to ligate an adaptor to the 3' end of the first strand of cDNA and then a double stranded cDNA is synthesized. The resulting cDNA population contains a mix which is representative of all of the mRNA. This cDNA population can be stored and used for experiments rather than storing the mRNA which is much more unstable. The novel technique of ligating an adaptor uses a partially double stranded adaptor with a degenerate overhang to hold the adaptor in conjunction with the first strand of cDNA. This results in a much more efficient ligation. A polymerase chain reaction is performed with cDNA, using as primers one primer specific to the cDNA of interest and one primer complementary to the adaptor. The resulting amplified DNA is hybrid captured using an oligomer probe specific for the gene of interest, this oligomer being 5' to the oligomer used to prime specifically the polymerase chain reaction. This hybrid captured DNA is purified and then subjected to another round of polymerase chain reaction, this time using a set of nested primers which are internal to those used for the primary round of PCR. By nested primers are meant primers which are more internal, i.e., more toward the middle of the gene, than the previously used primers which are therefore more 5' and more 3' than are the nested primers. Again, one primer will be specific to the gene of interest and the other primer will be complementary to the adaptor which had been added to the cDNA. This latter primer will not be the same as the one used earlier but will be complementary to a more 3' region of the adaptor. Each round of amplification and the step of hybrid capture enrich for the gene of interest.

These series of steps are necessary for easy success in locating gene ends. In theory one could possibly design a gene specific oligomer for the reverse transcription step which results solely in the production of the specific cDNA of interest. In practice this is far from true, the cDNA population which is produced consisting of DNA complementary to a wide variety of genes. The cDNA of interest will be only a small percentage of the total cDNA. Amplifying the cDNA with a different gene specific primer will further enrich for the cDNA of interest, but again in practice only a portion of the amplified DNA is that of interest. Hybrid capture using yet a different complementary region of the gene again enriches for the cDNA of interest, and finally one more round of amplification with yet another gene specific primer will once again enrich the population. At this stage it is very likely that a discrete band of DNA will appear on a gel when the amplified cDNA is electrophoresed. If this is cloned or sequenced it is highly likely that any clone chosen will contain the cDNA of interest. This method prevents the necessity of having to subclone the initial cDNA product and then to screen the resulting cDNA library for the gene of interest.

Another aspect of the invention is the novel technique for ligating adaptors to an end of a nucleic acid, this technique preventing the loss of material from the end which is commonly encountered when other techniques of ligation are utilized. This novel technique is fully adaptable to ligating adaptors at either a 5' or a 3' end and can be used with any nucleic acid, e.g., with RNA, cDNA, or genomic DNA.

DESCRIPTION OF THE INVENTION

Figure 1:
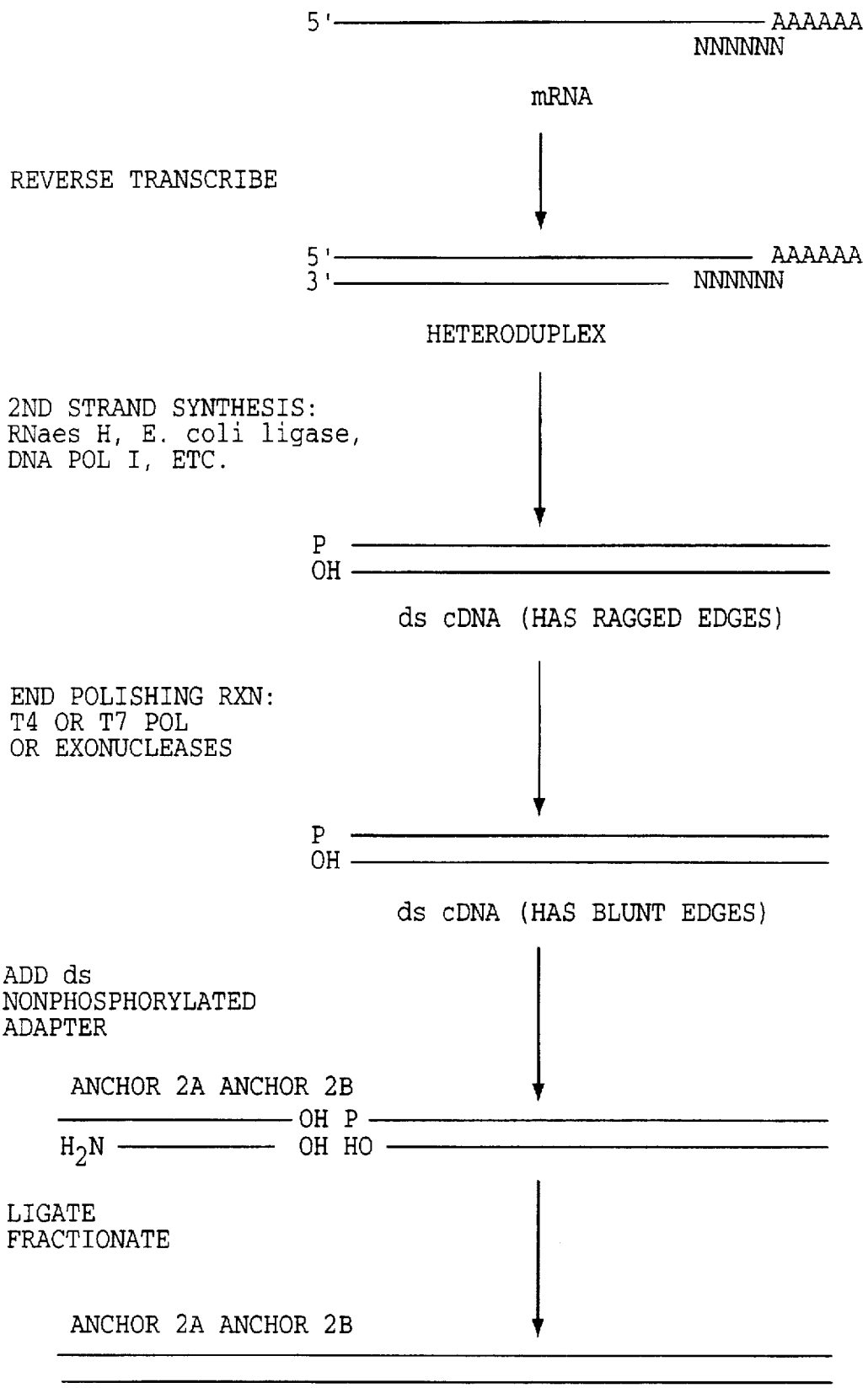
FIG. 1 illustrates the initial steps involved in a 5' hybrid capture RACE procedure. Messenger RNA is reverse transcribed using a degenerate primer (NNNNNN), the RNA is destroyed, a second strand is synthesized, and the resulting ds cDNA is polished to give blunt ends. A double stranded adaptor is blunt end ligated to the 5' end of the ds cDNA.
Figure 2A:
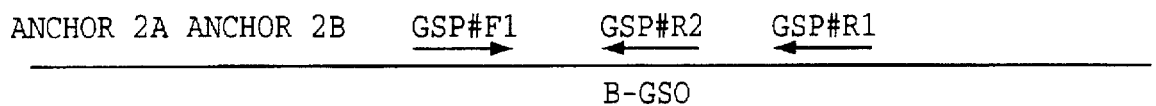
FIG. 2A illustrates an example of the relative positions of all of the oligomers used in the late steps of a 5' hybrid capture RACE procedure.
Figure 2B:
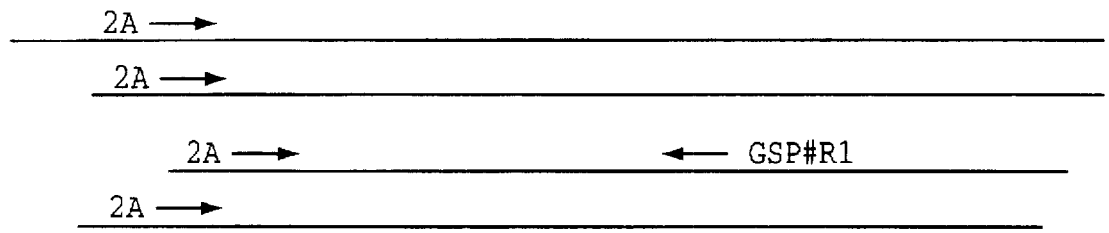
FIG. 2B illustrates the late steps involved in a 5' hybrid capture RACE procedure. Beginning with ds cDNA with an adaptor on the 5' end, PCR is performed using GSP#R1 and anchor 2A as primers. The amplified DNA is hybrid captured using a biotin labeled gene specific probe shown as B-GSO. A second round of PCR is carried out using the nested primers GSP#R2 and anchor 2B. This yields ds cDNA highly enriched for the gene of interest.
Figure 2B:
Figure 2B:
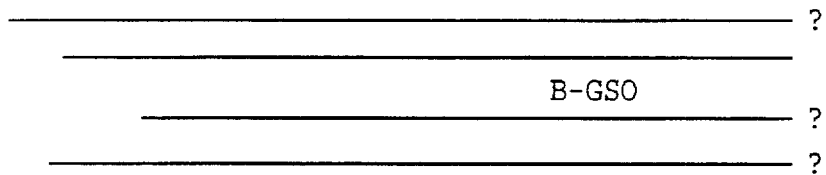
Figure 2B:
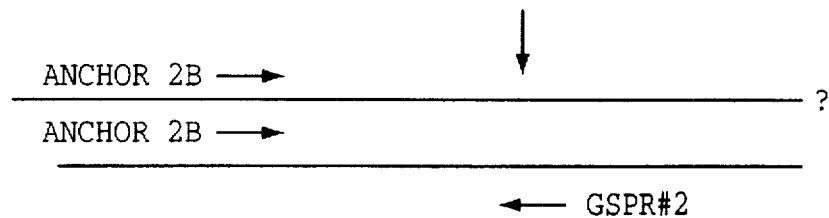
Figure 2B:
Figure 2B:
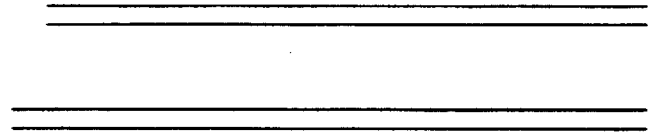

The invention is designed to purify a cDNA of interest. The method can be biased such that either the 5' end or the 3' end of the cDNA is included in the final purified product. Advantage is made of two separate polymerase chain reactions plus an intervening solution hybridization step to enrich further for the cDNA of interest. These enrichment steps eliminate the necessity of having to subclone the cDNA as a cDNA library and then to screen the resulting library for a clone containing the cDNA of interest. The method in brief outline involves the steps of 1) purifying mRNA, 2) reverse transcribing the mRNA to form a heteroduplex, 3) treating the heteroduplex to destroy the RNA and then forming a double stranded cDNA (ds cDNA), 4) adding a specific tail (called an anchor) to the ds cDNA, 5) amplifying the cDNA via PCR, 6) hybrid capturing the amplified cDNA, and 7) performing a second round of PCR using different primers. The method can be modified to result in a cDNA which contains either its 5' end or its 3' end. Several variations are possible for each step, these variations often being a matter of personal preference. Some variations are detailed in the examples below.

A second aspect of the invention involves a novel technique of ligating an adaptor to the end of a nucleic acid so as to preserve the end of said nucleic acid for further study. There are two commonly used alternative methods at the present time for preparing ds cDNA. One alternative is to copy MRNA to make a first strand of cDNA and then to use a combination of RNase H and DNA polymerase to synthesize the second strand of cDNA. The RNase H nicks the RNA and allows for the DNA polymerase to fill in as in a nick translation reaction, using the nicked RNA as primer. Unfortunately this method does not allow for priming at the extreme 5' end of the cDNA and it is common to lose 30–40 nucleotides from this end which had been in the first strand of cDNA but which could not be copied into the second strand. The second alternative is to ligate a single stranded oligomer directly onto a single stranded piece of DNA using the enzyme T4 RNA ligase. This method allows one to recover the 5' end without loss of sequence. Nevertheless, this is an extremely inefficient reaction, being only about 1% efficient and often resulting in complete failure.

The novel method of adding an adaptor to the ends of a nucleic acid so as not to lose any sequence from the end is approximately 75% efficient. The method involves forming a first strand of DNA, mixing this with a nucleic acid consisting of a short strand and a long strand wherein the short strand is complementary to the 5' end of the long strand and wherein the 3' end of the long strand is a degenerate sequence. This degenerate sequence can overlap and hybridize with the 3' end of the single stranded piece of cDNA causing the 5' end of the short strand to abut the single stranded 3' end. A ligation is performed and because the long strand holds the short strand next to the single strand the ligation is very efficient, much more efficient than an ordinary blunt end ligation of two double stranded fragments. No bases are deleted from the end of the single strand. A primer complementary to the short strand is used to prime synthesis of the second strand of cDNA.

Variations of this novel ligation scheme can also be performed to preserve the 3' end of a gene. One variation involves attaching an anchor sequence to the 5' end of an oligo dT or random primer which is used to prime the first strand synthesis of cDNA using mRNA as a template. This incorporates the anchor beyond the 3' end of the gene, and upon synthesizing the second strand of cDNA the complete 3' end remains intact.

It is a simple matter to combine the methods to add anchors at both the 5' and 3' ends. This not only preserves both ends of the gene but inserts known sequences at the ends which can be used for PCR, sequencing or cloning purposes. This can be useful in preparing cDNA libraries.

The present invention is described with reference to the following Examples, which are offered by way of illustration and are not intended to limit the invention in any manner. Standard techniques well known in the art or the techniques sepcifically described below are utilized.

EXAMPLE 1

HYBRID CAPTURE 5' RACE

I. Purification of poly A+mRNA.

Purification of mRNA is a technique well known to those of skill in the art. The exact methods used for purification depend on the organism or cell type from which the mRNA is to be obtained. Briefly, the cells are lysed, DNA is digested with RNase free DNase, total RNA is either ethanol precipitated or banded in CsCl, and mRNA is purified from total RNA by chromatography on an oligo(dT)-cellulose or poly (U)-Sepharose column (Berger, S. L., *Methods in Enzymology* 152:215–219 (1987); MacDonald, R. J. et al., *Methods in Enzymology* 152:219–227 (1987); Jacobson, A., *Methods in Enzymology* 152:254–261 (1987)). One should prepare mRNA using a method most suitable for the cell type they are using.

II. First Strand cDNA Synthesis

Purified poly A+ mRNA is precipitated and redissolved at 250 ng/µl in 5 mM HEPES pH 7.5, 0.1 mM EDTA. This RNA is denatured by mixing 8.0 µl (2.0 µg) with 0.9 µl 100 mM methyl mercury hydroxide and warming at 65° C. for 5 minutes. This is neutralized by addition of 0.9 µl 350 mM β-mercaptoethanol. The resulting solution is vortexed and centrifuged briefly in a microfuge to spin down the drops. Neutralization is allowed to occur for at least 1minute. The first strand synthesis reaction is prepared by mixing 8.0 µl of reverse transcription primer (the primer must not be phosphorylated at the 5' end), 8.2 µl H$_2$O 8.0 µl 5×BRL RT buffer (reverse transcription buffer from Bethesda Research Laboratories), 2.0 µl 100 mM dithiothreitol, 1.6 µl 10 mM dNTP mix, and 0.4 µl RNasin. This is warmed to 37° C. and then Superscript II reverse transcriptase is added at 1.0 µl per µg RNA. This is warmed at 37° C. for 60 minutes. The reaction is stopped by addition of 1.0 µl 500 mM EDTA and warming at 65° C. for 10 minutes. The amount of reverse transcriptase primer used in this reaction will vary depending on the specific primer. Final primer concentrations in the range of 1–30 µM are normally used. The expected yield is 0.2–0.4 µg of first strand per µg of input mRNA when a random primer is used and 0.5–1.0 µg when an oligo dT primer is used.

III. Second Strand Synthesis

A. Cleanup of first strand synthesis

The first strand synthesis reaction is fractionated on a Sepharose CL-4B column (Eschenfeldt, W. H. and Berger, S. L., *Methods in Enzymology* 152:335–337 (1987)). This separates high from low molecular weight material and will remove unincorporated dNTPs, excess primers and other low molecular weight material. The high molecular weight fractions are pooled. If the column is run using a buffer of 10 mM Tris pH 7.4, 10 mM KCl, 0.1 mM EDTA the pooled fractions can be used directly in the following step. Otherwise, ethanol precipitate the nucleic acid and resuspend in the said buffer.

B. Synthesis of the 2d strand

Mix 1 µg heteroduplex cDNA produced in the first strand synthesis, 40 µl 10×1 for-all buffer (this is 250 mM Tris acetate pH 7.7, 500 mM potassium acetate, 100 mM magnesium acetate), 4.0 µl 1 M ammonium sulfate, 20.0 µl 100 mM dithiothreitol, 10.0 µl 2 mM dNTP mix (prepare a dNTP mix at about 1.0 Curie/millimole in $^{32}$P dATP which is 1.5×10$^6$ disintegrations per minute (dpm) per microgram of second strand or 0.82×10$^6$ dpm/µg of ds cDNA), 4.0 µl 15 mM NAD (nicotine adenine dinucleotide), 4 µl 10 mg/ml bovine serum albumin, 1.6 µl RNase H at 1 unit/µl, 2.0 µl *E. coli* ligase at 2 units/µl, DNA polymerase I at 10 units/µl, and H$_2$O to give a final volume of 400 µl. Incubate this at 14° C. for 8–16 hours. Stop the reaction by addition of 10 µl 500 mM EDTA. The ds cDNA is then purified. Any type of purification step can be used, a wide variety of columns for such purposes being commercially available. The Qiaquick PCR cleanup procedure has been found to work well. This column is eluted with approximately 50 1µl of 10 mM Tris pH 8.5, 1.0 mM EDTA. This second strand synthesis step converts the heteroduplex cDNA quantitatively to ds cDNA.

IV. 5' end polishing

In practice the step of second strand synthesis leaves many cDNA molecules with ragged ends, i.e., they are not fully double stranded at both ends but may have an overhang of single stranded region. This polishing step removes any single stranded ends of the cDNA. Polishing is accomplished by mixing 2.0 µg ds cDNA, 10.0 µl 10–1 for-all buffer, 1.0 µl 100 mM dithiothreitol, 3.0 µl 10 mM dNTP mix (yielding 300 µM of each dNTP), 1.4 µl 1.5 mM NAD, 4.0 µl RNase A at 1 ng/µl, 1.6 µl RNase H at 1 unit/µl, 4.0 µl *E. coli* ligase at 2 units/µl 1.65 µl T4 DNA polymerase at 4 units/µl, 1.34 µl T7 DNA polymerase at 10 units/µl, and bring to 100 µl volume with H2O . Incubate at 15° C. for 15 minutes then stop the reaction by addition of 3.0 µl 500 mM EDTA. Phenol:chloroform extract the mix and back extract with ammonium acetate:isopropanol with 1 µg of glycogen carrier. Rinse with 80% ethanol, dry in a lyophilizer, and resuspend the DNA in 10 µl of TE.

V. Adaptor ligation—Option 1

A. Adaptor preparation

An adaptor of known sequence is ligated to the end of the cDNA. See FIG. 1. This adaptor is used to design two nested primers to be used in the two rounds of PCR which are performed in later steps of the invention. The adaptor consists of two complementary strands of DNA. The "top" strand of the adaptor, which corresponds to the mRNA strand, is synthesized such that it is a normal strand of DNA with a 3' OH group. The "lower" strand of the adaptor, corresponding to the first strand of cDNA synthesized, is made such that it has a 5' OH group and a 3' NH$_2$ group. The adaptor is added as follows: the two strands of the adaptor are added to a solution such that the final concentration of each is 25 µM. Add to this 2.0 µl 10×1 for-all buffer and bring to a total of 20 µl with H$_2$O. Incubate at 90° C. for 30 seconds, 65° C. for 5 minutes, then leave at room temperature for 5 minutes. This allows for hybridization of the two strands of adaptor to each other.

B. Ligation of the adaptor to the cDNA

The ligation reaction consists of mixing 10.0 µl of the cDNA preparation from above, 6.0 µl of the hybridized adaptors, 2.4 µl 10×1 for-all buffer, 3.0 µl 10 mM hexamine cobalt (III) chloride, 3.0 µl of a 0.5 mM ATP, 50 mM dithiothreitol mix, 0.75 µl of T4 DNA ligase at 400 units/µl (New England Biolabs), and adjusting to 30 μl total volume with H₂O. Incubate at 14° C. for 18 hours. Add EDTA and heat kill the reaction. C. Clean-up of the ligated cDNA Fractionate the ligated cDNA on a Sepharose CL-4B column to remove excess primers and other low molecular weight impurities. Pool the high molecular weight fractions. If the column is run using 10 mM Tris pH 8.4, 10 mM KCl, 0.1 mM EDTA the pooled fractions can be used directly in the following PCR without precipitation.

VI. Hybrid Capture 5' RACE

A. First Polymerase Chain Reaction

Perform a standard polymerase chain reaction on the cDNA with the attached adaptor. Polymerase chain reaction protocols are well known to those of skill in the art. See M.A. Innis et al., *PCR Protocols: A Guide to Methods and Applications* (Academic Press, Inc., New York (1990)). If several different cDNA preparations with attached adaptors were prepared, the one with the greatest abundance of the desired gene is chosen. The abundance of cDNA in the various preparations can be tested by performing limiting dilution analysis PCR using two gene specific primers, e.g., GSP#R1 and GSP#F1 as shown in FIG. 2. Since the object is to recover the 5' end of the gene, these two primers should be near the 5' end of the already known sequence, roughly 100 base pairs apart from each other. Limiting dilution analysis PCR is simply performing PCR on a series of dilutions of a sample and determining how much the sample can be diluted and still show a discrete amplified band of DNA when the products are run on a gel. Once the best cDNA sample has been chosen perform PCR as follows: as one primer use a gene specific oligomer located approximately 100–200 bases from the 5' end of the already known sequence of the cDNA, this primer being shown as GSP#R1 in FIG. 2. The second primer is complementary to the 5' region of the ligated adaptor, this primer being shown as the region Anchor 2A in FIG. 2. It is preferable to use a hot start PCR. The preferred conditions are to use TaqPlus DNA polymerase with 1×C-PCR buffer (20.0 mM TrisHCl pH 9.0, 8.5 mM NaCl, 10.0 mM KCl, 10.0 mM (NH₄)₂SO₄, 2.0 mM MgSO₄, 0.1% Triton X-100). PCR conditions are 95° C. for 30 seconds followed by cycles of 96° C. for 4 seconds, 65°–70° C. (depending on the primers) for 10 seconds, and 72° C. The 72° C. time depends on the length of the expected product, leaving this extension reaction at 72° C. for 1 minute per kilobase of length of the longest expected product.

It is useful to set up the PCR as a cycle titration, using 0.2–2.0 ng of cDNA as the substrate for each reaction. Trace label these by making the reaction solutions approximately 0.1 Curie/millimole in dATP so that quantification can be performed at later steps. Several PCRs are performed to titrate between 18 to 30 cycles. Run each of the titrations on an agarose gel and choose the number of cycles which gives an even, nonsaturated smear as the substrate for the next step. The reactions will often show bands, but these are likely to be spurious unless the transcript was quite abundant. The amplified product from the best titration cycle is then purified. This can be done by gel purifying on an agarose gel, recovering DNA from the region of 500–5000 base pairs, or by chromatography on a CL-4B or CL-6B column. The DNA is ethanol precipitated, dried, and resuspended in TE. The DNA concentration can be determined from the specific activity of the DNA.

Gene specific enrichment is calculated at this stage by limiting dilution analysis PCR. Use two gene specific oligomer primers for this. These can be GSP#R2 and GSP#F1 as shown in FIG. 2. This result is compared with the value determined from the limiting dilution analysis PCR previously performed on the initially synthesized cDNA solution to determine whether enrichment has occurred.

B. Hybrid Capture

The amplified DNA is enriched in the product of interest, but in practice it will be only a small percentage, quite possibly only a fraction of 1%, of the amplified material. This is especially true if the specific mRNA was of low abundance. A hybrid capture step can result in a fairly dramatic enrichment for the cDNA of interest, enrichments of at least 10–100 fold commonly being seen and enrichments of 100–1000 fold sometimes being seen. Hybrid capture is performed by preparing a biotin labeled gene specific oligomer (B-GSO) (see FIG. 2), hybridizing this in solution with the amplified cDNA which has been denatured, and capturing the cDNA bound to the B-GSO with a magnet. This is a known technique, wherein the biotin binds to streptavidin which is attached to paramagnetic particles and it is these which are attracted to the magnet while holding the biotin which in turn is attached to the gene specific oligomer which is hybridized to the cDNA of interest. Unbound molecules can be washed away. The only amplified cDNA which is captured is that which hybridizes with the biotin labeled gene specific oligomer. Other spuriously amplified DNA or DNA which by chance was complementary to GSP#R1 (which had been used as the specific primer for PCR) but is not complementary to B-GSO will be washed away. The specific steps for hybrid capture are as follow: mix 5–50 ng of the primary amplified cDNA into a solution consisting of final concentrations of 10 mM sodium phosphate pH 7.0, 1 mM EDTA, 2.4 M tetraethyl ammonium chloride, and 0.1 nM of the biotin labeled gene specific oligomer. This is conveniently done by first preparing a 50×capture mix consisting of 79.0 μl H₂O, 1.0 μl B-GSO at 1 μM, 100.0 μl 1 M sodium phosphate pH 7.0 and 20.0 μl 500 mM EDTA. Mix 2.0 μl of this 50×capture mix with 18.0 μl amplified cDNA containing 5–50 ng of the cDNA and 80.0 μl 3 M tetraethyl ammonium chloride (Sigma). Incubate this at 90° C. for 5 minutes followed by 25° C. (or room temperature) for 60 minutes. To this add 10.0 μl washed streptavidin paramagnetic particles (Dyna) (the beads are washed in a solution (bead wash and stringency wash solution) consisting of 1×capture mix, 2.4 M tetraethyl ammonium chloride and diluted 5 fold in this same solution). Leave at 25° C. (room temperature) for 60 minutes with occasional stirring. Capture the beads with a magnet. Add 100.0 μl of the stringency wash solution to resuspend the beads and incubate at 35° C. for 10 minutes. Recapture with a magnet. Wash the captured beads twice with 100.0 μl of 10.0 mM Tris pH 8.7, 50 mM KCl, 0.1 mM EDTA at room temperature. Resuspend the beads in 15.0 μl of 5 mM Tris pH 8.7, 0.1 mM EDTA.

C. Second Polymerase Chain Reaction

A second round of PCR is performed using the hybrid captured cDNA as the template. A pair of nested primers, internal to the primers used for the first round of PCR, is to be used. The 3' primer is a gene specific primer, shown as GSP#R2 in FIG. 2. The 5' primer, called Anchor 2B as shown in FIG. 2, is complementary to the adaptor, but will be internal (3') to Anchor 2A. PCR is then carried out as with the first round of PCR. Again, it is preferred to use hot start PCR, to do a cycle titration of 18–30 cycles, trace label the reactions by including approximately 0.1 Curie/ millimole dATP, and check the reaction products on a gel. This round of PCR is likely to yield discrete bands and these correspond to the gene of interest. This amplified material can be gel purified and cloned or sequenced directly. If material is limiting it can simply be reamplified. If a smear is seen instead of a discrete band, choose the number of cycles which gives an even, nonsaturated smear and run on an agarose gel to purify size fractions or chromatograph on a CL-4B or CL-6B column and clone and sequence the products.

EXAMPLE II

HYBRID CAPTURE 5' RACE USING AN ALTERNATIVE METHOD TO LIGATE THE ADAPTOR

Figure 3:
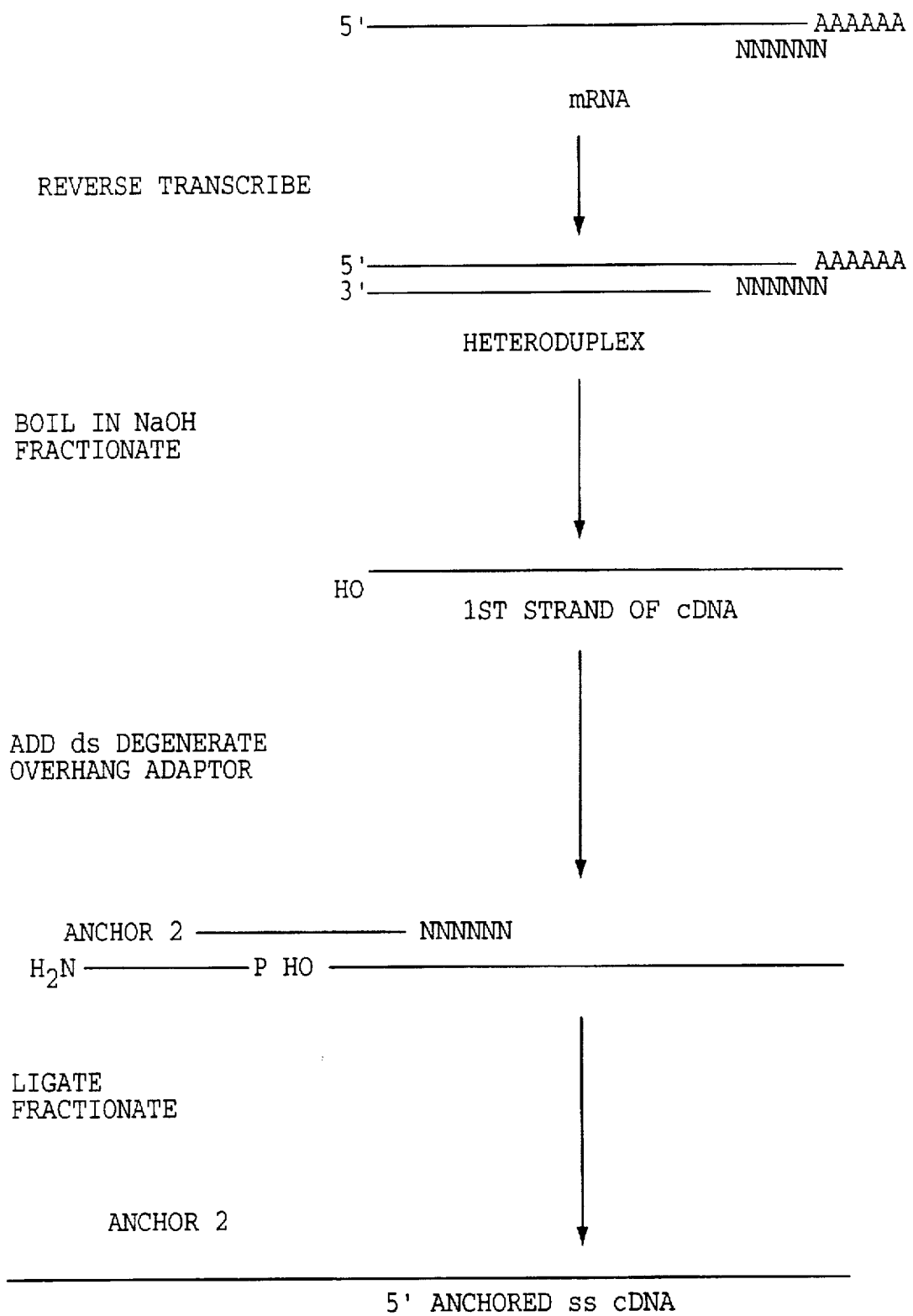
FIG. 3 illustrates a novel technique for ligating an adaptor to a nucleic acid without losing a portion of the end of the nucleic acid. A first strand of cDNA is synthesized and this is hybridized with an adaptor which has a degenerate overhang. The overhang on the upper strand holds the lower strand in close proximity to the 3' end of the first strand of cDNA. This allows for efficient ligation of the lower strand of the adaptor to the 3' end of the first strand of cDNA. The Figure illustrates the need to have a phosphorylated 5' end of the lower strand of the anchor. This lower strand also has an amine group at the 3' end. These groups are necessary to allow proper ligation while preventing unwanted ligation.

It is easy to imagine several variations on the procedure of hybrid capture 5' RACE as detailed in Example I. The present example outlines one such variation and is illustrated by FIG. 3. Here a first strand of cDNA is synthesized complementary to purified mRNA. The MRNA is hydrolyzed, then rather than performing the normal procedure to prepare the second strand of cDNA, a new procedure is carried out which results in ligation of the adaptor at the 3' end of this first strand. This method of ligating an adaptor onto the first strand of cDNA preserves the 5' sequence of the gene for future study. Because it is generally very difficult to recover 5' ends this novel method is of great importance. Once the 3' end adaptor has been added, it can be used along with a gene specific oligomer to run a first round of PCR. This is followed by hybrid capture and a second round of PCR as in Example I. The steps are as follows:

I. Purification of mRNA. First Strand Synthesis of cDNA and Clean-up of the First Strand These steps are performed essentially as detailed in Example I, and the first strand is purified. To the heteroduplex cDNA add 1 volume of 300 mM NaOH, 30 mM EDTA. Incubate at 100° C. for 5 minutes to hydrolyze the RNA stand. Fractionate the reaction on a Sepharose CL-4B column and pool the high molecular weight fractions. Estimate the DNA concentration, precipitate the sample, and resuspend in TE at 100 ng/µl ss cDNA.

II. Ligation of the Adaptor

The adaptor will be covalently ligated at the 3' end of the first strand of cDNA. To accomplish this two partially complementary oligomers of unequal lengths are synthesized. The short strand must be phosphorylated at its 5' end and have a 3' $NH_2$ group and will be ligated to the first strand of cDNA. The longer oligomer is complementary to the shorter oligomer but in addition contains additional 3' sequence. This additional 3' sequence is a degenerate sequence. Because of this degeneracy, some of the longer oligomers will be able to hybridize to the sequence at the 3' end of the first strand of cDNA. See FIG. 3.

A. Adaptor Preparation

Mix 2.0 µl of 100 µM short adaptor which has been phosphorylated, 2.0 µl of the long adaptor with the degenerate 3' end, 2.0 µl 10×1 for all-buffer and bring to 20.0 µl total volume with H2O. Incubate at 90° C. for 30 seconds, 65° C. for 5 minutes, 55° C. for 5 minute leave at room temperature.

B. Ligation

Mix 10.0 µl of the 100.0 ng/µl ss cDNA, 2.0 µl of the adaptor preparation, 1.8 µl 10×1 for-all buffer, 2.0 µl 10 mM ATP/50 mM dithiothreitol mix, 0.2 µl 10 mg/ml bovine serum albumin, 0.5 1 T4 DNA ligase at 400 units/µl, and bring to 30.0 µl with H2O. Incubate at 37° C. for 18 hours (overnight). Add EDTA and heat kill the reaction.

II. First Round PCR. Hybrid Capture. Second Round PCR

These steps are performed essentially as in Example I. The difference is that here one is starting with ss cDNA with an adaptor on the 3' end. This is used for PCR by mixing with one primer complementary to the adaptor and one primer specific for the gene, preferably one which is 5' to the primer used to synthesize the first strand. The amplified ds cDNA is then hybrid captured and subjected to a second PCR using nested primers, one complementary to a portion of the adaptor and one which is gene specific.

EXAMPLE III

HYBRID CAPTURE 3' RACE

The invention is well suited to recovering cDNA containing the 3' end of the gene rather than the 5' end. In the previous examples, the 3' end of the gene was lost as gene specific nested primers located 5' of the 3' end were used in the amplification steps. The procedure is here modified to produce a cDNA with an adaptor on the 3' rather than the 5' end of the gene. Primers for the amplification steps will be complementary to this adaptor which is beyond the 3' end of the gene. In this way the 3' end of the gene is not deleted by the amplification steps.

I. Purification of mRNA Messenger RNA is purified as stated in Example I.

II. First Strand Synthesis

Figure 4:
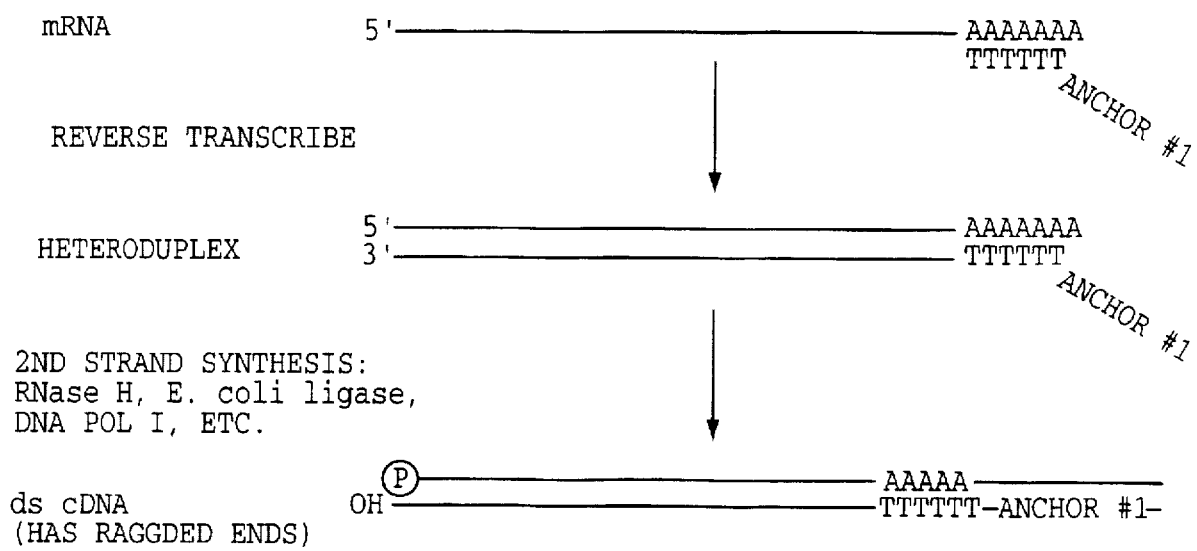
FIG. 4 illustrates a method for attaching an anchor beyond the 3' end of a gene. A primer is synthesized which has an anchor at its 5' end and oligo dT at its 3' end. This primer is used to prime the first strand synthesis of cDNA.

The first strand of cDNA is synthesized as in Example I except that rather than using a gene specific oligomer to prime the reaction, the primer is oligo dT which has the adaptor (anchor) attached at its 5' end. This is shown in FIG. 4. This allows the first strand to include the poly A tail and the very end of the 3' coding sequence.

III. First Round of PCR

Figure 5:
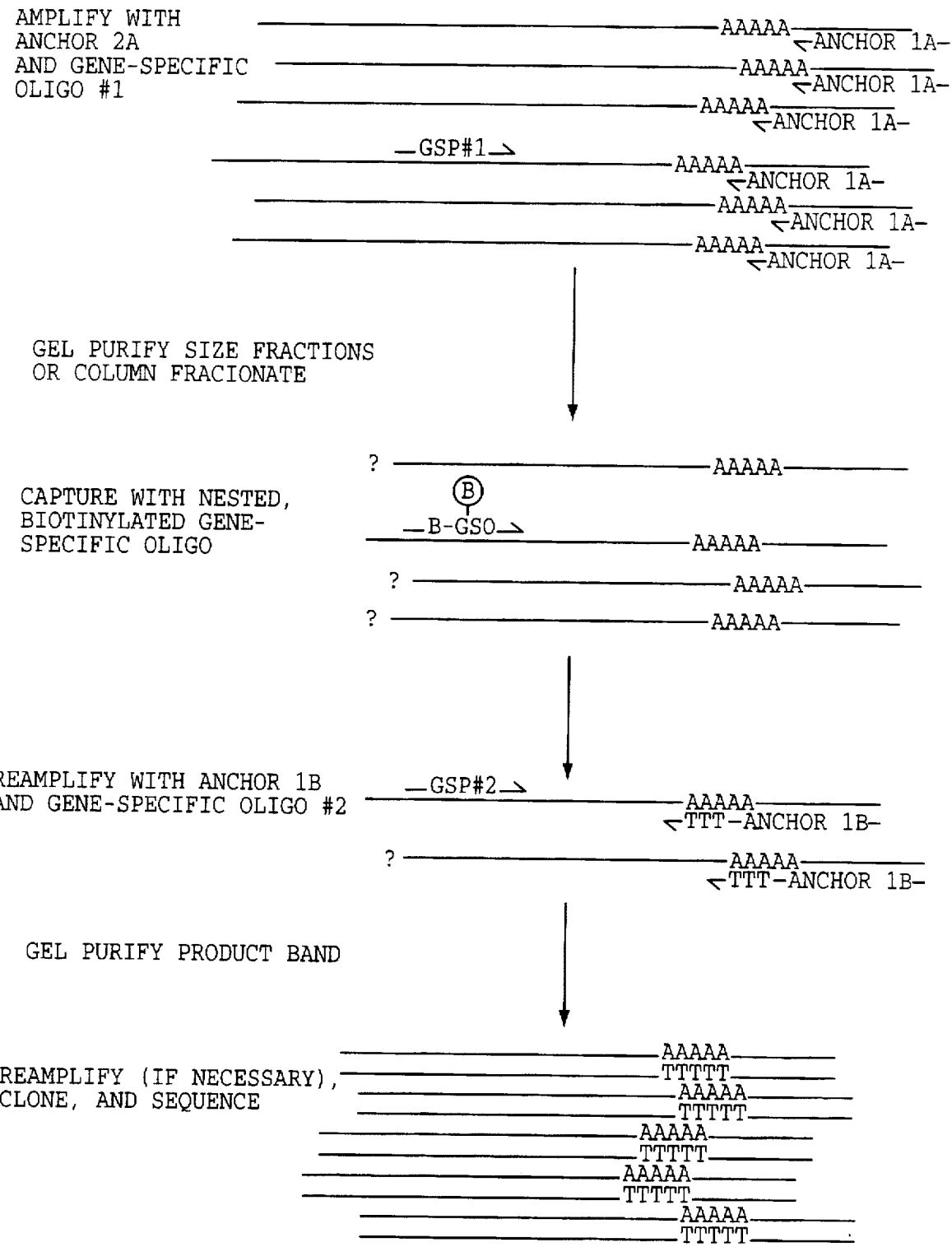
FIG. 5 illustrates one method of 3' hybrid capture RACE. Here an adaptor consisting of anchors 1A and 1B was added to the 3' end of a cDNA. The ds cDNA was amplified using a gene specific oligomer (GSP#1) for one primer and designing a strand complementary to anchor 1A for the second primer. The amplified DNA was captured by hybrid capture with a biotin labeled gene specific probe. Finally, the captured DNA again is amplified via PCR, using a second gene specific probe (GSP#2 located 3' to GSP#1) as one primer and designing a strand complementary to anchor 1B for the second primer. The amplified ds cDNA includes the 3' end of the gene.

The first round of PCR is performed as in Example I. Here the 3' primer will be complementary to the 3' end of the top strand of the adaptor (Anchor 1A) and the 5' primer will be a gene specific oligomer toward the 5' end of the cDNA as shown in FIG. 5.

V. Hybrid Capture

The amplified ds cDNA is purified and hybrid captured as in Example I. The biotin labeled gene specific oligomer is complementary to a region toward the 5' end of the gene as shown in FIG. 5.

VI. Second Round of PCR The second round of PCR is performed as in Example I. One primer will be a gene specific primer located 3' to the gene specific primer used in the first PCR. The second primer (Anchor 1B) will be complementary to the adaptor but will be 5' to Anchor IA. The resulting amplified cDNA contains the 3' end of the gene.

EXAMPLE IV

HYBRID CAPTURE RACE WITH GENOMIC DNA

All of the preceding examples as well as the discussion have described the invention as being solely directed to use with cDNA. The invention is quite adaptable to use with other nucleic acid such as with genomic DNA. For this method, one purifies genomic DNA, denature the DNA, dephosphorylate the genomic DNA, prepare a gene specific oligomer primer, mix the dephosphorylated genomic DNA and single primer, and allow synthesis of a single strand as an extension of the primer. This is done by addition of the 4 dNTPs, DNA polymerase, buffers, etc. by methods well known to those skilled in the art. Following this first strand synthesis, an adaptor is ligated to the 3' end. The adaptor is designed to have a 3' amino group to prevent it from ligating to the 5' end of any free primer or newly synthesized DNA. The anchor may ligate to 3' ends of genomic DNA, but such pieces of DNA will amplify in only a linear fashion during the following PCR and will result in only minor "impurities". A PCR is then performed using a gene specific oligomer as one primer and an oligomer complementary to the adaptor as the second primer. Successive steps of hybrid capture and a second round of PCR with nested primers are accomplished as in Example I.

The disclosed invention illustrates a new technique to purify and analyze rapidly the ends of genes. It obviates the need for library screening. It can be biased to result in purification of either a 5' end or a 3' end of a gene. The method can be performed using cDNA or genomic DNA. The technique uses 3 steps of enrichment—two separate rounds of PCR and a hybrid capture step. These steps result in production of a product which may be so enriched in the desired product that the final DNA produced may be sequenced without cloning. In some instances it may be necessary to clone the product, but it is necessary to characterize only a few clones to find one of interest. This can easily be done by preparing DNA minipreps and sequencing this miniprep DNA. The method is rapid and by eliminating the necessity of library screening is much less labor intensive than earlier methods of finding and studying genes.

Many modifications of this procedure will be apparent to those of skill in the art. Only a few of the possibilities have been described herein. Obvious modifications which have not been presented are considered to be equivalent to the disclosed methods.

What is claimed is:

1. A method for ligating an adaptor to an end of a nucleic acid, said method comprising:

a) preparing a single stranded nucleic acid;

b) preparing two strands of an adaptor wherein one strand is a shorter strand and one strand is a longer strand and wherein said shorter strand is complementary to a 5' end of said longer strand and wherein a 3' end of said longer strand is degenerate;

c) mixing said longer strand and said shorter strand to form a partially double stranded and a partially single stranded adaptor;

d) mixing said adaptor with said single stranded nucleic acid to allow said 3' end of said longer strand of said adaptor to hybridize with said single stranded nucleic acid; and e) ligating said adaptor with said single stranded nucleic acid.

2. A method for obtaining a 5' end of a gene, said method comprising the steps of:

a) purifying mRNA from an organism or cultured cells;

b) synthesizing a first strand of cDNA;

c) ligating an adaptor to the 3' end of said first strand of cDNA wherein said ligating is performed by the method of claim 1;

d) synthesizing a second strand of cDNA to create a ds cDNA using a primer complementary to said adaptor;

e) amplifying said ds cDNA to produce amplified cDNA by a first round of PCR wherein one primer is complementary to said adaptor and a second primer is a gene specific oligomer;

f) hybrid capturing said amplified cDNA wherein a gene specific oligomer is used to hybrid capture said amplified cDNA;

g) performing a second round of PCR wherein primers used for said second round of PCR are nested primers compared to primers used for said first round of PCR and further wherein one primer for said second round of PCR is a gene specific oligomer and a second primer for said second round of PCR is complementary to said adaptor.

* * * * *